United States Patent
Stem et al.

(10) Patent No.: US 12,185,973 B2
(45) Date of Patent: Jan. 7, 2025

(54) PERCUTANEOUS ACCESS NEEDLE GUIDANCE SYSTEMS AND METHODS USING AN ACCESS NEEDLE AND GUIDANCE PAD

(71) Applicant: GYRUS ACMI, INC., Southborough, MA (US)

(72) Inventors: Jessica N. Stem, Coon Rapids, MN (US); Connor Tower, Hudson, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 665 days.

(21) Appl. No.: 17/109,886

(22) Filed: Dec. 2, 2020

(65) Prior Publication Data

US 2021/0161554 A1    Jun. 3, 2021

Related U.S. Application Data

(60) Provisional application No. 62/942,803, filed on Dec. 3, 2019.

(51) Int. Cl.
  *A61B 5/06* (2006.01)
  *A61B 7/00* (2006.01)
  (Continued)

(52) U.S. Cl.
  CPC ...... *A61B 17/3403* (2013.01); *A61B 17/3423* (2013.01); *A61B 17/3468* (2013.01);
  (Continued)

(58) Field of Classification Search
  CPC  A61B 2017/00039; A61B 2017/00115; A61B 2017/3413; A61B 2017/3425;
  (Continued)

(56) References Cited

U.S. PATENT DOCUMENTS

| | | | |
|---|---|---|---|
| 4,610,663 A | 9/1986 | Rosenberg | |
| 6,731,966 B1 * | 5/2004 | Spigelman | A61B 90/17 600/407 |

(Continued)

FOREIGN PATENT DOCUMENTS

| | | |
|---|---|---|
| CN | 114760943 A | 7/2022 |
| WO | WO-2011150358 A1 | 12/2011 |

(Continued)

OTHER PUBLICATIONS

"International Application Serial No. PCT/US2020/062901, International Preliminary Report on Patentability mailed Jun. 16, 2022", 10 pgs.

(Continued)

*Primary Examiner* — Keith M Raymond
*Assistant Examiner* — Neshat Baset
(74) *Attorney, Agent, or Firm* — Schwegman Lundberg & Woessner, P.A.

(57) ABSTRACT

A guidance system for performing a percutaneous access incision comprises an access needle comprising a shaft and a tip located at a distal end of the shaft, and a guidance pad comprising a dermal side, an outward side, an opening to receive the access needle, the opening extending between the dermal side and the outward side, and a feedback device viewable from the outward side to provide an indication of a depth of the tip beneath the guidance pad and a trajectory of the shaft from the opening. A method for planning guidance of an access needle into a patient in preparation for a minimally invasive surgical procedure comprises determining a location for an access point on the patient, positioning a guidance pad over the access point, inserting a tip of the access needle through the pad, and displaying guidance information on the guidance pad.

28 Claims, 8 Drawing Sheets

(51) Int. Cl.
*A61B 17/34* (2006.01)
*A61B 17/00* (2006.01)

(52) U.S. Cl.
CPC ..... *A61B 5/062* (2013.01); *A61B 2017/00039* (2013.01); *A61B 2017/00115* (2013.01); *A61B 2017/3413* (2013.01); *A61B 2017/3425* (2013.01); *A61B 2017/3492* (2013.01)

(58) Field of Classification Search
CPC .... A61B 2017/3492; A61B 2017/3407; A61B 2090/3945; A61B 2034/107; A61B 90/13; A61B 17/3403; A61B 17/3423; A61B 17/3468; A61B 5/062
See application file for complete search history.

(56) References Cited

U.S. PATENT DOCUMENTS

| | | | |
|---|---|---|---|
| 9,737,232 B2 | 8/2017 | Fan | |
| 2006/0229641 A1 | 10/2006 | Gupta et al. | |
| 2008/0269600 A1 | 10/2008 | Csavoy et al. | |
| 2010/0094116 A1* | 4/2010 | Silverstein | A61B 5/061 606/108 |
| 2011/0282188 A1* | 11/2011 | Burnside | A61B 34/25 600/424 |
| 2016/0008074 A1* | 1/2016 | Glossop | A61B 90/11 606/130 |
| 2017/0196591 A1* | 7/2017 | Long, Jr. | A61B 17/3403 |
| 2017/0303940 A1 | 10/2017 | Sperry et al. | |
| 2018/0228568 A1 | 8/2018 | Kato et al. | |
| 2018/0303559 A1* | 10/2018 | Shepherd | A61B 6/12 |
| 2020/0121287 A1* | 4/2020 | Nakamura | H04W 88/00 |
| 2021/0212658 A1* | 7/2021 | McGrath | A61B 34/25 |

FOREIGN PATENT DOCUMENTS

| | | |
|---|---|---|
| WO | WO-2017120477 A1 | 7/2017 |
| WO | WO-2021113371 A1 | 6/2021 |

OTHER PUBLICATIONS

"International Application Serial No. PCT/US2020/062901, International Search Report mailed Mar. 31, 2021", 6 pgs.

"International Application Serial No. PCT/US2020/062901, Written Opinion mailed Mar. 31, 2021", 8 pgs.

\* cited by examiner

PERCUTANEOUS ACCESS NEEDLE GUIDANCE SYSTEMS AND METHODS USING AN ACCESS NEEDLE AND GUIDANCE PAD

CROSS-REFERENCE TO RELATED APPLICATION

This application claims the benefit of priority to U.S. Provisional Patent Application Ser. No. 62/942,803, filed Dec. 3, 2019, the contents of which are incorporated herein in their entirety.

TECHNICAL FIELD

This document pertains generally, but not by way of limitation, to surgical instruments and methods for inserting and guiding instruments used to perform percutaneous medical procedures. More specifically, but not by way of limitation, the present application relates to systems and methods for inserting and guiding minimally invasive insertion instruments such as laparoscopic access needles.

BACKGROUND

Many surgical procedures involve the treatment or removal of subdermal target tissue, e.g., diseased or unwanted tissue or growths, located inside of a patient. As such, these procedures require access to the internal anatomy of the patient via an open procedure or through a smaller opening in minimally invasive procedures. In minimally invasive procedures, a surgeon guides an insertion instrument, such as an access needle, into the epidermis of the patient along a trajectory to introduce a tip of the access instrument into a surgical site within a chest or abdominal cavity of the patient. Imaging of the anatomy of the patient can be used to plan the trajectory of the insertion needle. However, interpretation of the imaging and placement of the access needle can be difficult such that sometimes an interventional radiologist performs the access needle placement rather than the surgeon that performs the medical procedure.

Examples of surgical instruments are described in U.S. Pat. No. 4,610,663 to Rosenberg; U.S. Pat. No. 9,737,232 to Fan; and Pub. No. US 2017/0303940 A1 to Sperry et al.

Overview

The present inventor has recognized, among other things, that problems to be solved in performing medical procedures include the inconvenience of a surgeon having to utilize an interventional radiologist to perform access needle insertion. Use of such specialists significantly prolong the surgical procedure because the access needle is typically placed the day before the medical procedure by the interventional radiologist. Furthermore, the present inventor has recognized that use of real-time guided navigation of access instruments is typically not feasible due to impracticality of using imaging equipment in real time, including exposure of the patient and surgeon to radiation. Additionally, movement and breathing of the patient can make interpretation of still images and real-time imaging of the patient difficult.

The present subject matter can provide solutions to these problems and other problems, such as by providing systems and methods that include instrument guidance pads that can provide real-time feedback of the location and orientation of an access instrument during the placement procedure. The instrument guidance pads can include hardware for displaying indicia that can be updated in real-time indicative of the location of a surgical instrument such as an access needle. The guidance pad can react directly to the presence of the access needle such that a separate imaging system is not required. In examples, the guidance pad can further provide guidance information, such as a desired orientation of the access needle and no-go zones for the access needle. In examples, the guidance pad can include sensors for providing indicia of tissue and anatomy of the patient. Methods of performing surgical procedures with such guidance pads are also described herein.

In an example, a guidance system for performing a percutaneous access incision can comprise an access needle comprising a shaft and a tip located at a distal end of the shaft, and a guidance pad comprising a dermal side, an outward side, an opening to receive the access needle, the opening extending between the dermal side and the outward side, and a feedback device viewable from the outward side to provide an indication of a depth of the tip beneath the guidance pad and a trajectory of the shaft from the opening.

In another example, a method for planning guidance of an access needle into a patient in preparation for a minimally invasive surgical procedure comprises determining a location for an access point on the patient, positioning a guidance pad over the access point, inserting a tip of the access needle through the pad, and displaying guidance information on the guidance pad.

In an additional example, a guidance pad for guiding an access needle into a patient in preparation for a minimally invasive surgical procedure comprises a dermal side, a outward side, a opening to receive the access needle, the opening extending between the dermal side and the outward side, and an array of light emitters surrounding the opening and viewable from the outward side to provide an indication of a depth of a tip of the access needle beneath the guidance pad and a trajectory of a shaft of the access needle from the opening, wherein each of the light emitters of the array has a variable property.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
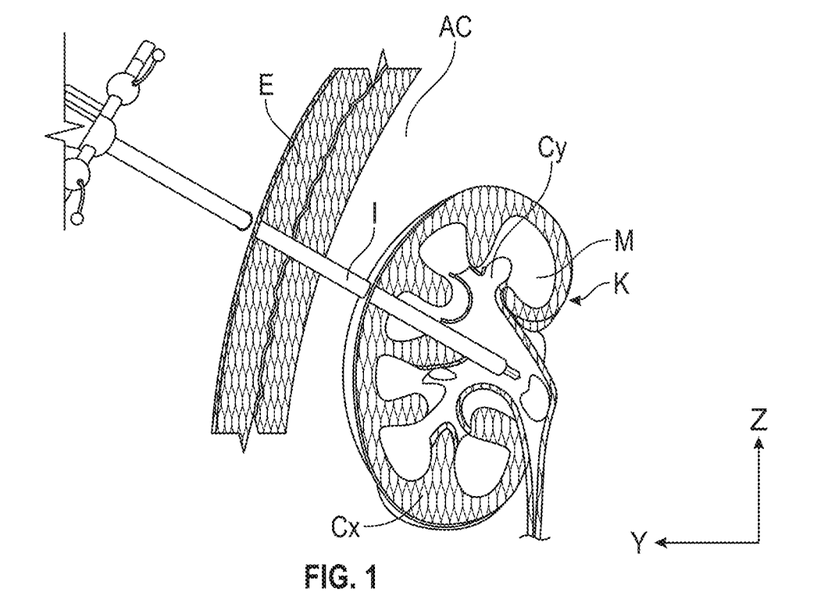
FIG. 1 is a schematic illustration of a kidney in an abdominal cavity taken in a coronal plane.
Figure 2:
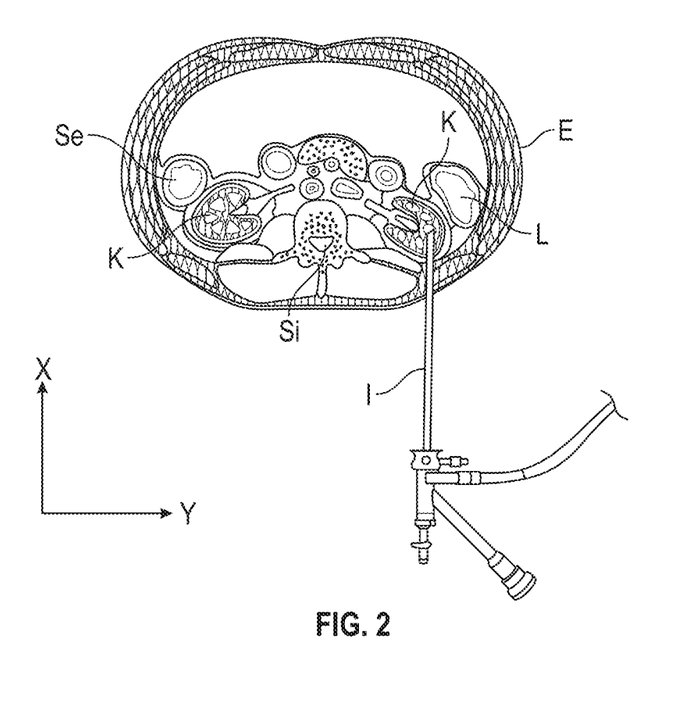
FIG. 2 is a schematic illustration of kidneys in an abdominal cavity taken in a transverse plane.

FIG. 1 is a schematic illustration of kidney K in abdominal cavity AC taken in a coronal plane. The coronal plane can be defined by axis Y in the medial-lateral direction and axis Z in the superior-inferior direction. FIG. 2 is a schematic illustration of kidneys K in abdominal cavity AC taken in a transverse plane. The transverse plane can be defined by axis Y in the medial-lateral direction and axis X in the anterior-posterior direction. FIGS. 1 and 2 are be discussed concurrently.

Abdominal cavity AC can be defined by epidermal layers E that provide a barrier to access of kidney K. Instrument I can be inserted through epidermal layers E and into kidney K. Kidney K can comprise outer cortex Cx, medulla M and calyces Cy. Kidney stones can form in kidney K is various places, particularly in calyces Cy. A surgical procedure to remove kidney stones can comprise use of stone fragmentation and stone retrieval devices that are inserted through an opening in epidermal layers E provided by an access needle. The access needle can be used to provide orientation to a guide tube, such as a laparoscope. As such, in order to perform a surgical procedure to remove kidney stones, the access needle must be blindly guided into kidney K through epidermal layers E and into calyces Cy, typically using only two-dimensional imaging. As such, the surgeon must mentally interpret the imaging and transfer desired position and orientation information from the imaging onto the patient to find the kidney and avoid other organs. As can be seen in FIG. 1, the orientation of instrument I in the coronal plane can be influenced by the location of calyces Cy where kidney stones typically form. As can be seen in FIG. 2, the orientation of instrument I in the transverse plane can be influenced by the location of spine Si and other organs, such as the lungs, liver L and spleen Se. Thus, the initial trajectory of an access instrument used to place instrument I in abdominal cavity AC is important. Placement of the access instrument can be further complicated by movement or breathing of the patient.

The present disclosure provides systems and method for providing indicia and feedback regarding the location of instruments relative to the space underneath epidermal layer E and the locations of anatomy of the patient. The systems and methods can include the use of a guidance pad that can provide real-time feedback to a surgeon, or other personnel, regarding the orientation and depth of the instrument, particularly the tip, relative to the guidance pad and the anatomy of the patient. Note, although the present application is described with reference to nephrolithotomy procedures, the systems and methods of the present disclosure can be used in other procedures, such as those used to remove tumors including laparoscopic tumor ablation procedures.

Figure 3:
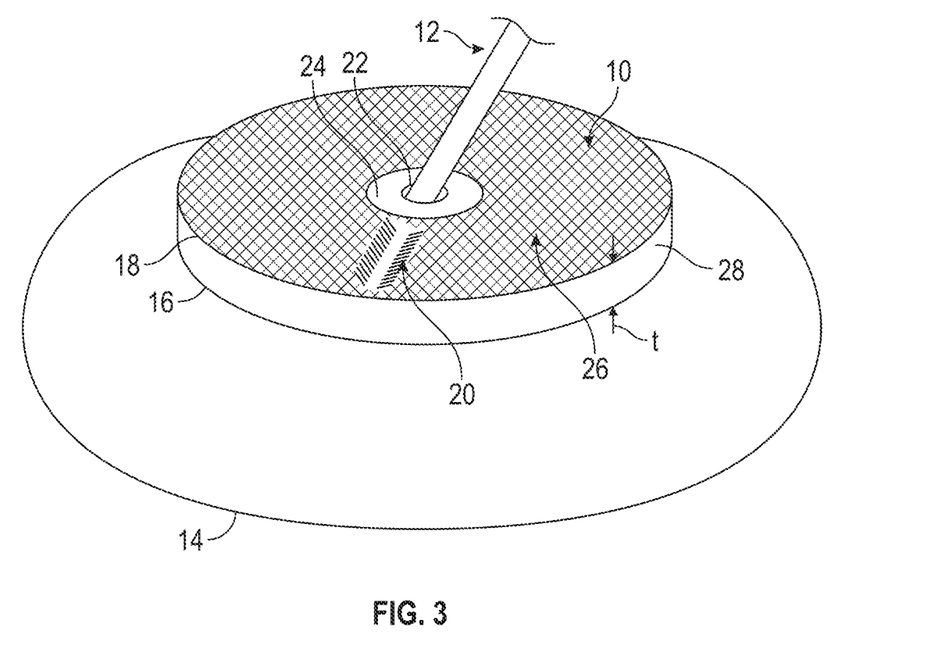
FIG. 3 is a schematic illustration of a guidance pad of the present disclosure being used to orient an access needle into an abdominal cavity.

FIG. 3 is a schematic illustration of guidance pad 10 of the present disclosure being used to orient access needle 12 into an abdominal cavity underneath skin 14 of a patient. Pad 10 can comprise a mat having inner (dermal side) surface 16 that can be placed against skin 14 and outer (outward indicia) surface 18 from which indicia 20 can be read by an operator or user of guidance pad 10. Pad 10 can comprise port 22 through which access needle 12 can positioned.

Guidance pad 10 can be made of a uniform material or can be made of a plurality of layers. Thickness t of guidance pad 10 can correspond to the construction of guidance pad 10. It can be desirable to minimize thickness t in order to increase pliability and flexibility of guidance pad 10 such that guidance pad 10 can conform to the contours of skin 14. Indicia 20 can be formed by a layer of pad 10 or by additional components added to outer surface 18, as discussed in greater detail with respect to FIGS. 5 and 7. Guidance pad 10 can additionally include an adhesion layer to abut skin 14 to immobilize guidance pad 10 relative to the patient. Guidance pad 10 can be configured to be disposable or reusable. As such, guidance pad 10 can include additional protective layers to encapsulate components for forming indicia 20, such as light emitters or a display screen, to facilitate cleaning and sterilization and the reapplication of an adhesive layer.

Port 22 can comprise an opening through guidance pad 10 from inner surface 16 to outer surface 18. Port 22 can be reinforced with ring 24 to provide port 22 with rigidity and a size to match that of access needle 12. Thus, the internal diameter of ring 24 can be minimized to match the size of needle 12 to maximize the display area of outer surface 18 and to provide some holding (immobilizing) capability of needle 12. In the illustrated example, access needle 12 and port 22 are circular. However, needle 12 and port 22 can be provided with other shapes, matching or otherwise. Likewise, in the illustrated example, guidance pad 10 has a circular outer perimeter. However, the outer perimeter of guidance pad 10 can have other shapes. A circular outer perimeter of guidance pad 10 can be useful for providing uniform information relative to port 22; for example, all portions of the outer perimeter of wall 28 can be equidistant from port 22. Guidance pad 10 can be sized to cover a surface are of the patient sufficient to cover the distance between a desired incision point in the patient and target tissue where treatment is to be performed, such as the location of a tumor or kidney stones. As such, port 24 need not be located at the center of guidance pad 10, but can be located at a periphery to maximize the distance between access port 24 and the periphery. Such a configuration can be useful in procedures where the general direction of the target anatomy from the access incision is known.

Outer surface 18 can be provided with markings 26 to facilitate interpretation of indicia 20. For example, markings 26 can comprise a grid system, a Cartesian coordinate system, a polar coordinate system and the like. Port 22 can be the origin of the coordinate systems. Indicia 20 can be provided on markings 26 to provide multiple pieces of information regarding access needle 12. In particular, indicia 20 can provide 1) an indication of the distance that a tip of access needle 12 (not visible in FIG. 3) is from port 22; 2) an indication of the trajectory of access needle 12 relative to port 22; and 3) an indication of the depth of the tip of access needle 12 below guidance pad 10. The visual information provided by indicia 20 can be in the form of color-coded light or light of different intensities, as discussed with reference to FIGS. 4-8, or in the form of images or illustrations provided on a display screen, as discussed with reference to FIG. 9.

Figure 4:
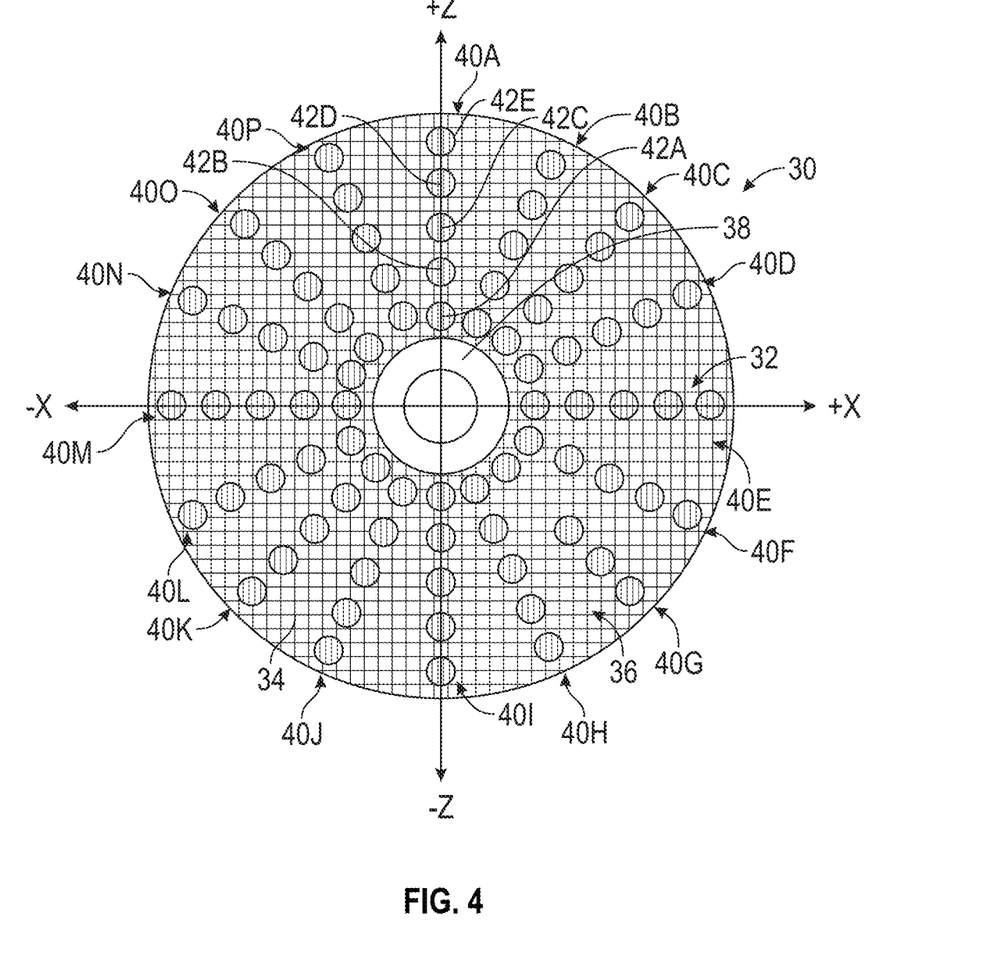
FIG. 4 is a top view of a first example of a guidance pad using light-emitting diodes to provide depth and distance feedback.

FIG. 4 is a top view of guidance pad 30 comprising array 32 of light-emitting elements that can be configured to provide depth and distance feedback to a user of guidance pad 30. Guidance pad 30 can comprise an example of guidance pad 10 of FIG. 3. Guidance pad 30 can comprise outer surface 34, markings 36 and port 38. Array 32 of light-emitting elements can include a plurality of individual light emitters that are arranged in an organized pattern on outer surface 34 such that the way (e.g., pattern, intensity, color) the light emitters are lit up or not lit up can convey visual information to the user. Markings 36 can comprise a grid system, a Cartesian coordinate system, a polar coordinate system and the like, that can be configured to indicate two- or three-dimensional space relative to port 38.

In the illustrated example, array 32 defines a plurality of columns of light emitters extending radially from a center within port 38 and markings 36 comprise a Cartesian coordinate system including X and Z axes that can, for example, correspond to the X, Y and Z axes of FIGS. 1 and 2. The light emitters can light up to correspond to a position of an instrument inserted through port 38. In an example, each light emitter can be off (black in FIGS. 4, 6 and 8) when not conveying any position information. The light emitter can turn on to indicate the presence of the instrument below pad 30. The brightness or color of each light emitter can convey distance away from pad of the instrument. FIG. 4 illustrates sixteen columns 40A-40P of light emitters, each column having five light emitters. For example, column 40A can comprise light emitters 42A-42E. However, the particular number of light emitters in array 32 can vary in different embodiments depending on the granularity of information that is to be obtained. Likewise, the spacing between lines of the grid of markings 36 can vary in different embodiments depending on the granularity of information that is to be obtained.

As discussed, guidance pad 30 can be constructed in a variety of different ways to be reusable or disposable. In an example, light emitters of array 32 can comprise light-emitting diodes (LEDs) mounted to a flexible circuit comprising a layer of guidance pad 30. The LEDs can be sealed behind a protective layer. The flexible circuit can be coupled to an embedded controller or an external controller that can control operation of the LEDs based on the location of an instrument inserted into port 38. For example, the flexible circuit can include a magnetic field sensor for each of the LEDs and an instrument can include a magnet proximate the distal tip of the instrument. As such, the strength of the magnetic field detected by each magnetic field sensor can be influenced by the proximity of the distal tip of the instrument to each LED. The brightness or color of each LED can be programmed to change based on the proximity of the magnet. For example, for no magnetic field the LED can be off, for an adjacent magnet the LED can be on and fully bright. However, in other examples, the LEDs can be programmed to react to different inputs, such as ultrasonic information or other proximity sensor information.

Figure 5:
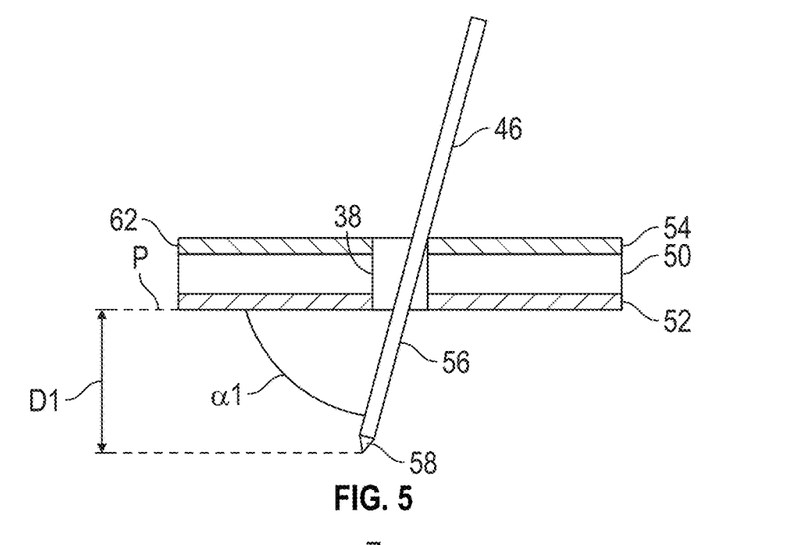
FIG. 5 is a side schematic view of an insertion needle inserted into the guidance pad of FIG. 4 at a first depth and a first orientation.
Figure 6:
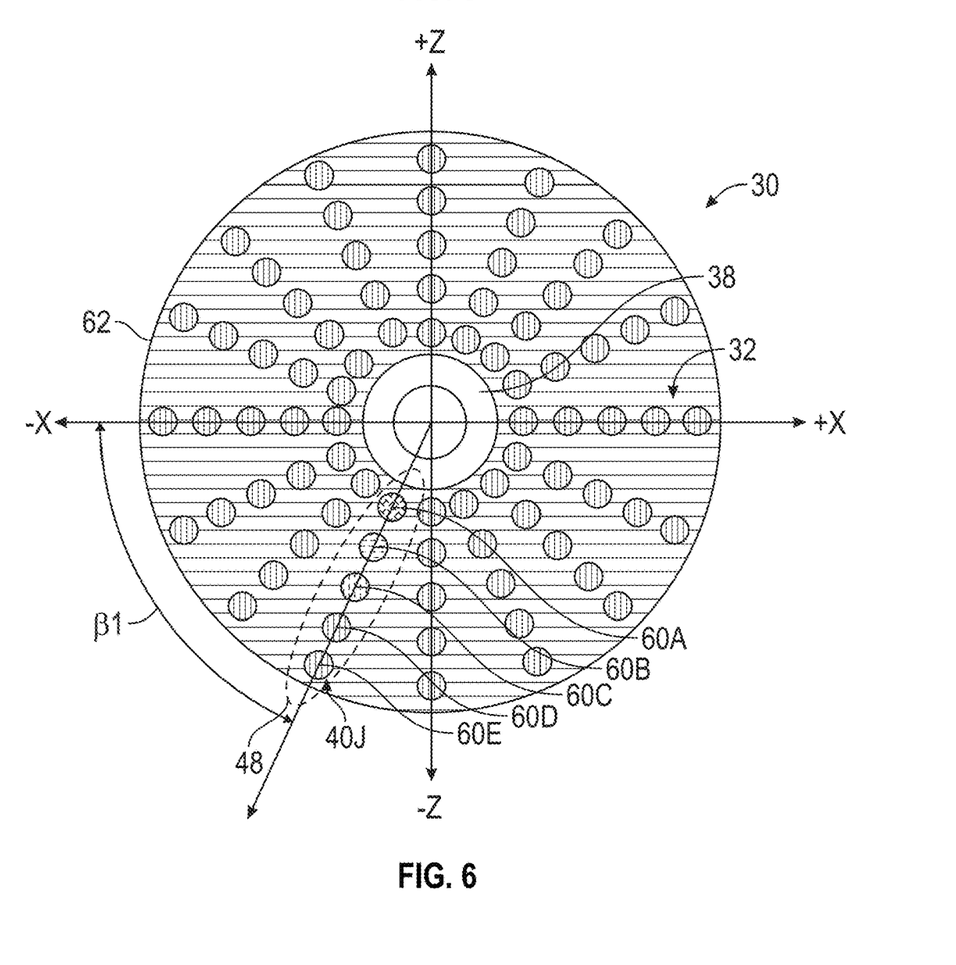
FIG. 6 is a top view of the guidance pad of FIG. 5 showing visual feedback indicative of the first depth and the first orientation.

FIG. 5 is a side schematic view of insertion needle 46 inserted into guidance pad 30 of FIG. 4 at a first depth, indicated by distance D1, and a first orientation, indicated by angle α1. FIG. 6 is a top view of guidance pad 30 of FIG. 5 showing visual feedback 48 indicative of the first depth and the first orientation. Guidance pad 30 can comprise backing 50, adhesive layer 52 and display layer 54. Insertion needle 46 can comprise shaft 56 and tip 58. FIGS. 5 and 6 are discussed concurrently.

Shaft 56 of insertion needle 46 can be inserted into port 38 such that tip 58 is positioned distance D below guidance pad 30. Shaft 56 can be angled relative to plane P of guidance pad 30 at angle α1. Array 32 of light-emitting elements can react to the location of shaft 56 and tip 58. In the example illustrated in FIG. 6, insertion needle 46 can be located closest to column 40J of array 32 such that light emitters of column 40J can comprise visual feedback 48. Column 40J can comprise light emitters 60A-60E. Column 40J can correspond to insertion needle 46 extending into port 38 at angle β1 relative to the X axis.

Activation of at least one of light emitters 60A-60E of column 40J can provide an indication of angle β1 for shaft 56. As can be seen in FIG. 5, shaft 56 is inserted into port 38 such that tip 58 does not extend to periphery 62 of guidance pad 30. As such, all of light emitters 60A-60E do not activate. For example, light emitters 60E and 60D closest to periphery 62 do not light up and light emitters 60A-60C closest to port 38 are activated. The degree to which light emitters 60A-60C are activated can provide an indication of both angle α1 and depth D1. For example, light emitter 60A can be activated a first degree to show the presence of the portion of shaft 56 just below guidance pad 30 and light emitter 60C can be activated a second degree to show the presence of tip 58 further below guidance pad 30. In an example, light emitter 60C can be brighter than light emitter 60A to indicate where the greatest depth of shaft 56 and to indicate where tip 58 is located. Light emitter 60B can be activated to a degree in between the first and second degrees such that a continuous spectrum or a gradual changing of light emitting activation can be provided. As mentioned in other examples, color can be used to indicate depth. For example, a heat map could be used where subsequently greater depth can be indicated by the colors blue, green, yellow and red.

Figure 7:
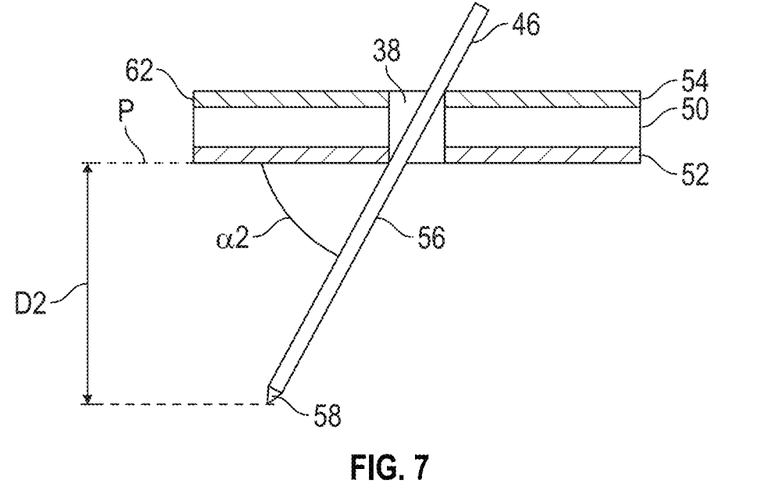
FIG. 7 is a side schematic view of an insertion needle inserted into the guidance pad of FIG. 4 at a second depth and a second orientation.
Figure 8:
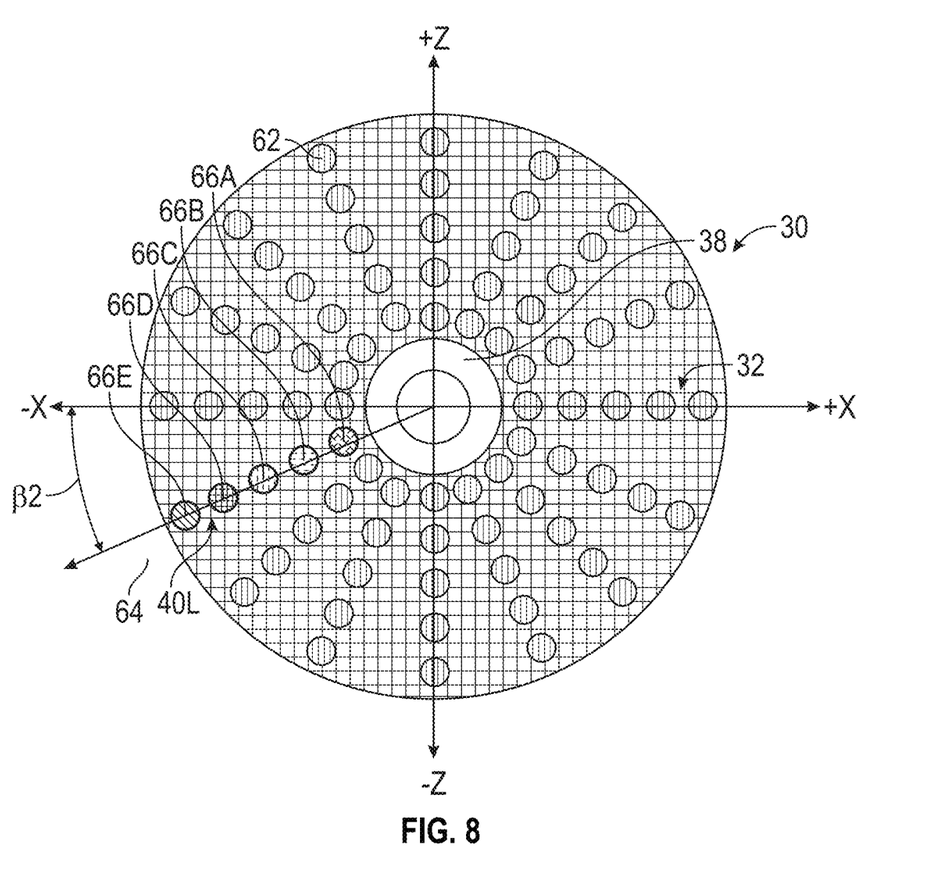
FIG. 8 is a top view of the guidance pad of FIG. 7 showing visual feedback indicative of the second depth and the second orientation.

FIG. 7 is a side schematic view of insertion needle 46 inserted into guidance pad 30 of FIGS. 5 and 6 at a second depth, indicated by distance DE, and a second orientation, indicated by angle α2. FIG. 8 is a top view of guidance pad 30 of FIG. 7 showing visual feedback 64 indicative of the second depth and the second orientation. FIGS. 7 and 8 are discussed concurrently.

Shaft 56 of insertion needle 46 can be inserted into port 38 such that tip 58 is positioned distance D2 below guidance pad 30, with D2 being greater than D1 of FIG. 5. Shaft 56 can be angled relative to the plane of guidance pad 30 at angle α2, with α2 being less than α1. In the example illustrated in FIG. 7, insertion needle 46 can be located closest to column 40L of array 32 such that light emitters of column 40L can comprise visual feedback 64. Column 40L can comprise light emitters 66A-66E. Column 40L can correspond to insertion needle 46 extending into port 38 at angle β2 relative to the X axis, with β2 being less than β1.

Activation of at least one of light emitters 66A-66E of column 40L can provide an indication of angle β2 for shaft 56. As can be seen in FIG. 7, shaft 56 is inserted into port 38 such that tip 58 extends to periphery 62 of guidance pad 30. As such, all of light emitters 66A-66E can be activated to some degree. For example, light emitter 60E closest to periphery 62 and light emitter 60A closes to port 38 can be activated in opposite manners to indicate the depth and orientation of shaft 56. The degree to which light emitters 66A-66D are activated can provide an indication of both angle α2 and depth D2. For example, light emitter 66A can be activated a first degree to show the presence of the portion of shaft 56 just below guidance pad 30 and light emitter 60E can be activated a second degree to show the presence of tip 58 further below guidance pad 30. In an example, light emitter 60E can be brighter than light emitter 60A to indicate where the greatest depth of shaft 56 and to indicate where tip 58 is located. Light emitters 60B-66D can be activated to varying degrees in between the first and second degrees such that a continuous spectrum or a gradual changing of light emitting activation can be provided.

Light emitters of array 32 can update in real-time to indicate the location and depth of tip 58 below plane P of guidance pad 30. Thus, as a surgeon can manipulate shaft 56 and can receive an indication of how far tip 58 is located below skin 14 (FIG. 3) of the patient. In an example, markings 36 can include a scale to convert indicia of the light emitters to an actual length. For example, with reference to light emitters 66A-66E of FIG. 8, black could indicate a depth of zero and white could indicate the full length of shaft 56 between tip 58 and a handpiece (now shown). In other examples, shaft 58 can be provided with markings that correspond to the depth and indicia from the guidance pad can be used to provide corroborating depth information along with orientation (e.g., angle α1 and angle β1) information. In another example, one of the light emitters can be pre-activated to a desired intensity or color to provide target depth and orientation information to which a surgeon is to guide tip 58. As such, guidance pad 30 can be configured to provide both passive and active guidance information. Furthermore, as discussed below with reference to FIGS. 9 and 10, guidance pads of the present disclosure can additionally be configured to provide passive and active anatomic information.

Figure 9:
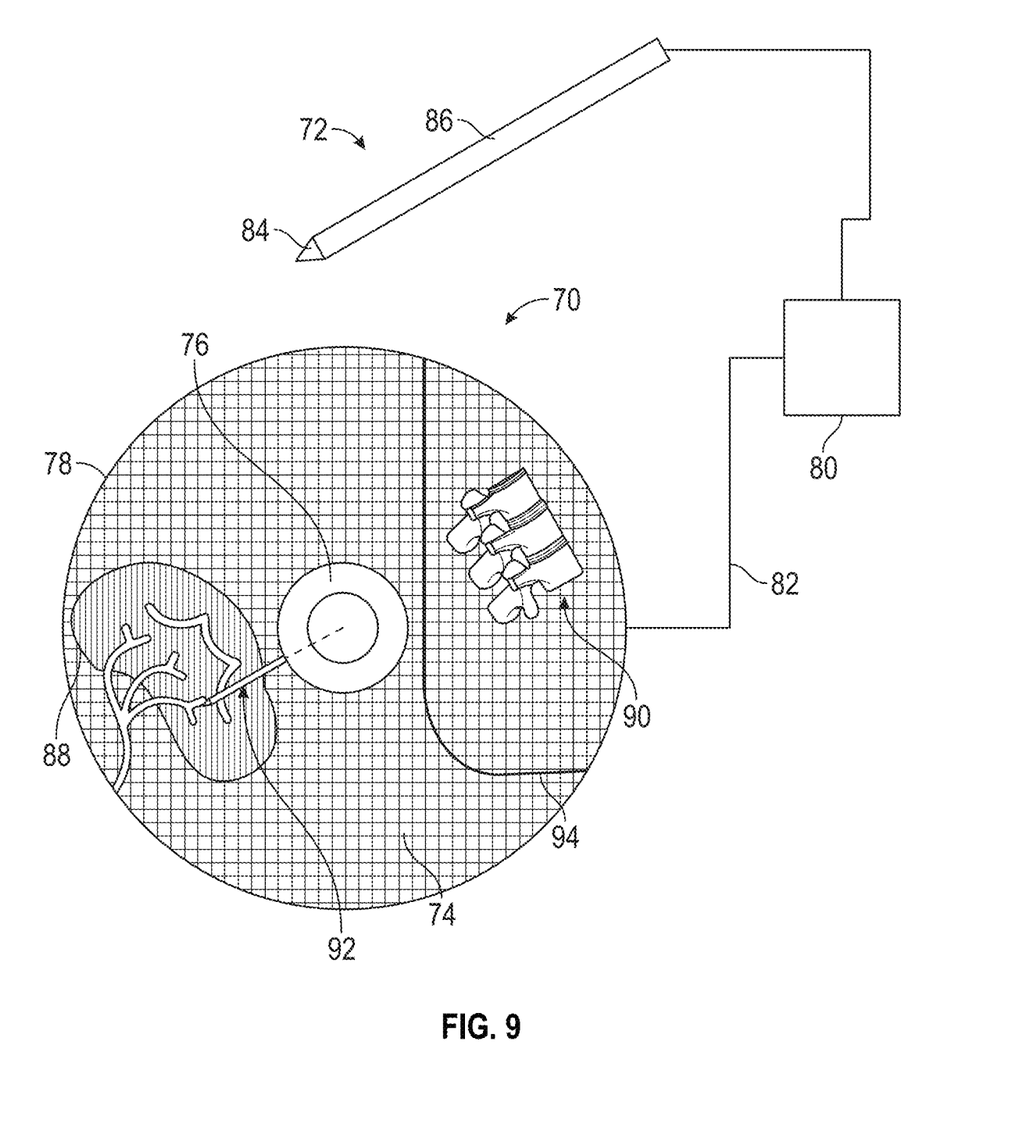
FIG. 9 is a top view of a second example of a guidance pad using an ultrasound-enabled insertion needle with a guidance pad incorporating a visual display.

FIG. 9 is a top view of guidance pad 70 incorporating a visual display being used in conjunction with sensor-enabled, e.g., ultra-sound-enabled, insertion needle 72. Guidance pad 70 can comprise an embodiment of guidance pad 10 of FIG. 3. Guidance pad 70 can comprise display screen 74 extending between port 76 and periphery 78. Guidance pad 70 can be connected to controller 80. Controller 80 can be connected to guide pad 70 via cable 82 or can be incorporated directly into guide pad 70. Insertion needle 72 can comprise top 84 and shaft 86.

Display screen 74 can comprise a layer of guide pad having the same shape as guide pad 70. Display screen 74 can be positioned above an adhesive layer and an electronics layer and below a protective layer. Display screen 74 can comprise an active display unit, such as a liquid crystal display, a plasma screen, an organic light-emitting diode display and the like. As such, display screen 74 can be configured to display images from different inputs utilizing controller 80. For example, controller 80 can receive input from sensor-enabled insertion needle 72. Controller 80 can interpret information contained in at least on of electronic, digital, and mechanical signals from sensor 96 (FIG. 10) and display images on display screen 74. The information from sensor-enabled insertion needle 72 can be used to interpret the position and orientation of shaft 86 and to generating imagery of tissue and anatomy surrounding insertion needle 72. For example, display screen 74 can show kidney 88, spinal column 90, instrument 92 and boundary 94.

Figure 10:
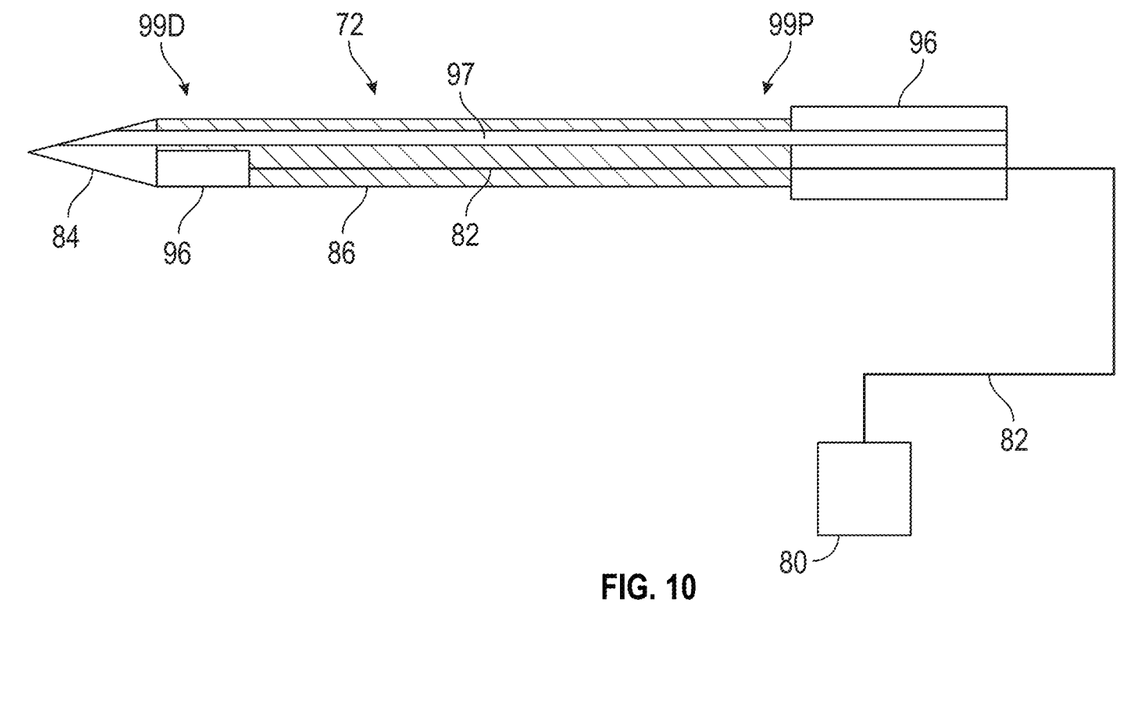
FIG. 10 is a schematic illustration of an insertion needle having a transducer for interacting with the guidance pad of FIG. 9.

FIG. 10 is a schematic illustration of insertion needle, or access needle, 72 having sensor 96 for interacting with guidance pad 70 of FIG. 9. Insertion needle 72 can comprise tip 84, shaft 86, sensor 96, lumen 97 and handpiece 98. Insertion needle 72 can be configured for use with any of the guidance pads disclosed herein.

Shaft 86 can extend from proximal end 99P to distal end 99D. Handpiece 98 can be located at or near proximal end 99P and can comprise any suitable device configured to facilitate insertion needle 72. In other examples, handpiece 98 can be omitted. Tip 84 can be located at distal end 99D of shaft 86. Tip 84 can be integral with shaft 86 or a separate piece. Tip 86 can comprise a device to facilitate puncturing of tissue, such as skin, e.g., epidermal layers E (FIGS. 1 and 2). Thus, tip 86 can comprise a sharp point, such as a needle point, or a sharp edge, such as a scalpel or razor blade. Lumen 97 can be configured to extend the length of insertion needle 72. Lumen 97 can extend through handpiece 98, shaft 86 and tip 84. However, lumen 97 can extend out of the side of shaft 86 without extending through handpiece 98. Likewise, lumen 97 can be configured to extend out of the exact distal end of tip 84 to more closely track with an incision point made with tip 84, but is shown offset for illustrative purposes. Lumen 97 can be used to insert other instrumentation into the patient after insertion needle 72 has been positioned in a desired location and orientation within a patient. For example, a guidewire can be placed into lumen 72 to mark the path of insertion needle 72. Thereafter, insertion needle 72 can be removed while the guide wire remains in place. Thus, the guidewire can be used to guide other instruments, such as dilator tubes and a laparoscope tube, to the surgical site determined by insertion needle 72.

Sensor 96 can be integrated into the construction of insertion needle 72. Sensor 96 can be included in shaft 86 or tip 84. Sensor 96 can be located at tip or proximate tip 84 or a predetermined or known distance from tip 84. In examples, tip 84 can be constructed of a sensor such that separate sensors and tips are not used. Sensor 96 can comprise a device configured to provide an indication of the location of tip 84. Sensor 96 can comprise a passive or active. In an example, top 84 can comprise a magnet that continuously emits a passive magnetic signal. In another example, sensor 96 can comprise an ultrasound transducer that selectively emits an active signal. In other examples, sensor 96 can comprise a position sensor or a proximity sensor, such as a capacitive sensor or a photoelectric sensor. In additional embodiments, sensor 96 can comprise a combination of different sensors. Controller 80 can be configured to receive output of sensor 96 either directly or indirectly with the use of additional receiving components. For example, controller 80 can be connected to magnetic field sensors (e.g., Hall effect sensors or microelectromechanical system (MEMS) sensors) associated light emitters of guidance pad 30. In the embodiment of FIG. 10, sensor 96 can be configured as an ultrasonic transducer, the output of which can be read by controller 80.

Returning to FIG. 9, with insertion needle 72 inserted into port 76 such that tip 84 is behind (relative to FIG. 9), guidance pad 70 can detect the presence of sensor 96 and can activate display screen 74 to show a visual rendition of shaft 54 as instrument 92. Likewise, the ultrasound output of sensor 96 can be used to obtain imaging of anatomy, such as a liver and spine, and show visual renditions of kidney 88 and spinal column 90 on display screen 74. As such, the guidance system provided by guidance pad 70 and insertion needle 72 can provide visual indicia of the location of tip 84 within a patient relative to anatomy of the patient. Furthermore, as discussed with reference to FIG. 11, guidance information relating to the desired orientation of insertion needle 72 as well as locations where insertion needle 72 should not be positioned, such as no-go zone indicated by boundary 94, can be included in a surgical plan that can be visually displayed on display screen 74.

Figure 11:
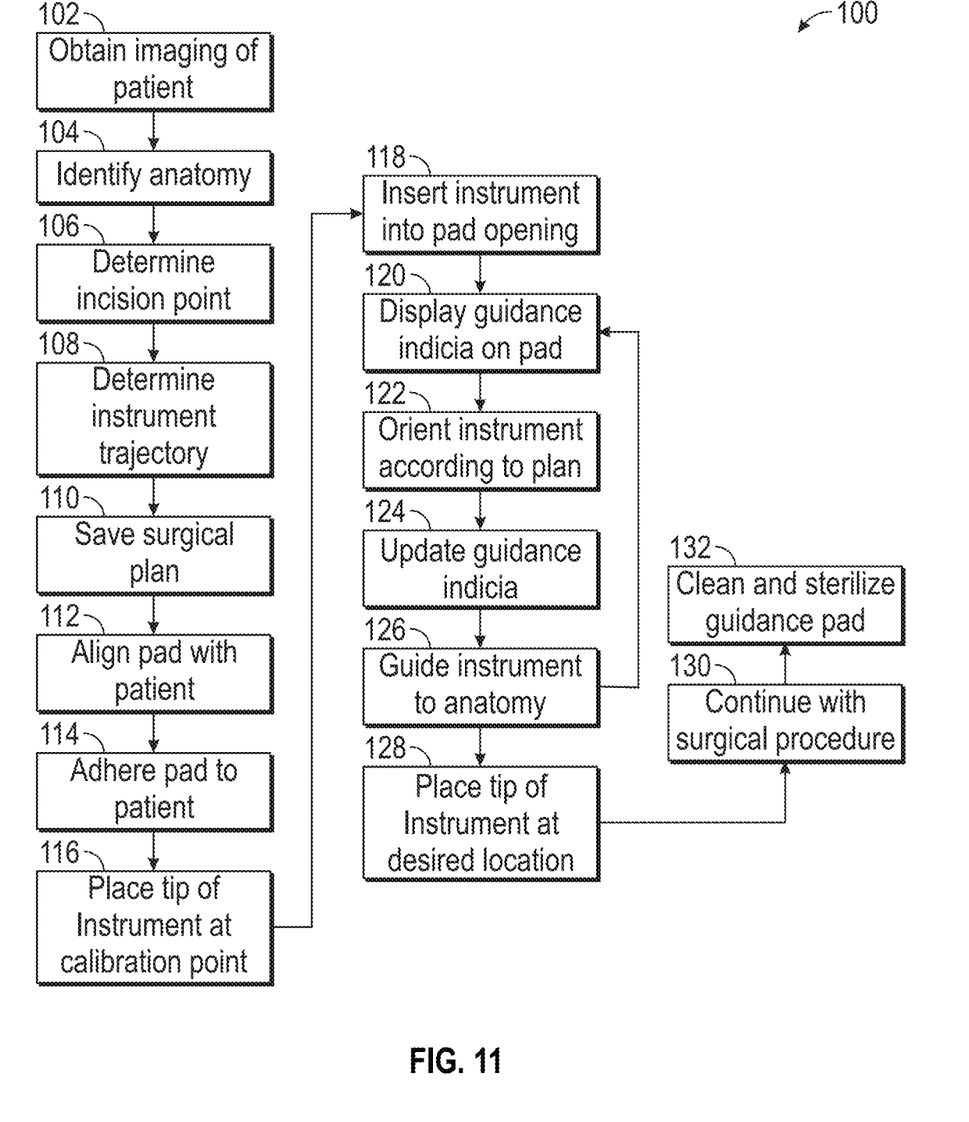
FIG. 11 is a schematic line diagram illustrating methods for performing surgical procedures using a guidance pad of the present disclosure to insert an access needle.

FIG. 11 is a line diagram illustrating method 100 for performing surgical procedures according the present disclosure. The surgical procedure can comprise an open procedure or a minimally invasive procedure. However, the disclosure is particularly well-suited for procedures making blind insertions of surgical instruments, such as laparoscopic procedures. FIG. 11 is discussed with reference to performing a Percutaneous Nephrolithotomy (PCNL) procedure using a laparoscope inserted into a tube placed with dilators and an insertion needle. In a PCNL procedure, kidney stones (nephrolithiasis) are removed from a kidney after being fragmented into small pieces suitable for extraction through the tube. Kidney stones of a variety of shapes and sizes typically form in the calyces of the kidney. As such, it is desirable to guide extraction instrumentation to the calyces to minimize movement and repositioning of the removal instrumentation or the need to produce a second insertion needle. Although FIG. 11 is described with reference to nephrolithotomy procedures, the systems and methods of the present disclosure can be used in other procedures, such as those used to remove tumors including laparoscopic tumor ablation procedures.

At step 102, medical images of a patient can be obtained. The medical images can be taken to obtain views of anatomy of the patient including a surgical location where an instrument is to be positioned. In particular, the abdominal cavity of the patient can be imaged to obtain views of a kidney and the locations of kidney stones within the kidney. The views can be taken in multiple planes, such as the coronal (Y-Z plane of FIG. 1), transverse (Y-X plane of FIG. 2) and sagittal planes. Three-dimensional imaging can also be obtained. Types of imaging that can be used include x-ray, Computed tomography (CT) scan, magnetic resonance imaging (MRI), ultrasound, and the like. The imaging can be obtained at the site where the surgical procedure is to be performed, such as a hospital, or at an outpatient facility.

At step 104, target anatomy in the imaging can be identified. For example, kidney K (FIG. 1) and kidney stones within kidney K can be identified. The locations of the kidney stones can be recorded and translated into three-dimensional coordinate locations, such as with respect to the X, Y and Z planes defined in FIGS. 1 and 2. The X, Y and Z coordinates can be determined by piecing together information from multiple two-dimensional imaging views of the patient.

At step 106, an incision point in the patient can be determined. The incision point can be a location on the epidermis of the patient where an access instrument, e.g., instrument I (FIGS. 1 and 2), access needle 12 (FIG. 3), access needle 46 (FIGS. 5 and 7) and insertion needle 72 (FIG. 10), can be positioned to reach the target anatomy, such as the calyces of the kidney, without intersecting any anatomy not intended to receive the access needle, such as the spine, liver and lungs. The location of the incision point can be recorded and translated into three-dimensional coordinate locations, such as with respect to the X, Y and Z planes defined in FIGS. 1 and 2.

At step 108, a trajectory for an insertion instrument can be determined. For example, the trajectory between the target anatomy and the incision point can be determined using the three-dimensional coordinate system. The trajectory of the instrument can be recorded and translated into three-dimensional coordinate locations, such as with respect to the X, Y and Z planes defined in FIGS. 1 and 2.

In other examples, the incision point can be determined by first planning a trajectory from the target anatomy to the epidermis (e.g., steps 106 and 108 can be performed in reverse order). In either example, the trajectory can be plotted to avoid intersecting other anatomy of the patient, such as the spinal column, liver, spleen and the like. Accordingly, no-go zones, such as the area cordoned off by boundary 94 in FIG. 9, can be identified and recorded in the three-dimensional coordinate system.

At step 110, a surgical plan can be saved including information specific to the patient and the target anatomy for performing the medical procedure. The surgical plan can include the locations of the target anatomy, the incision, the insertion instrument trajectory and the no-go zones. All of these pieces of information can be recorded as visual indicia that can be configured for display on a guidance pad for viewing by a surgeon during the surgical procedure.

The surgical plan can be saved electronically on a computer or machine readable medium. The term "machine readable medium" may include any medium that is capable of storing, encoding, or carrying instructions for execution by a machine and that cause the machine to perform any one or more of the techniques of the present disclosure, or that is capable of storing, encoding or carrying data structures used by or associated with such instructions. Non-limiting machine-readable medium examples include solid-state memories, and optical and magnetic media. In examples, the machine can be embodiments of guidance pads described herein, such as guidance pads 10, 30 and 70, or controller 80. In other examples, the machine can be a surgical imaging system, a surgical navigation system or a personal computer and the like. In examples, the surgical plan can be stored in a format for rendering a visual display to include indicia indicative of the patient, the anatomy, the target location, the incision location, no go zones, and the insertion instrument trajectory.

Steps 102-110 can describe a method of planning a surgical procedure. In particular, the steps can describe a method of planning an insertion of laparoscope for performing a PCNL procedure using an insertion or access needle.

At step 112, a guidance pad, such as one or more of guidance pads 10, 30 and 70, can be aligned with a patient. In particular, the planned incision point for the patient can be aligned with an opening in the guidance pad, such as ports 24, 38 and 76. Ports 24, 38 and 76 can thus act as registration points that register the coordinate system of the anatomy with the patient. For example, the planned incision point can be located visually on the outside of the patient by comparing with the imaging. Thus, the guidance pad can be placed on the patient to register the markings (e.g., the coordinate system provided by markings 26 or 36) with the patient. The patient can be appropriately anesthetized to perform the insertion procedure.

At step 114, the guidance pad can be attached to the patient. Step 114 can be optional. The guidance pad can be attached by adhesive backing provided on the guidance pad, such as for disposable pads, or an adhesive liquid applied to the back of the guidance pad, such as for reusable guidance pads. In examples using ultrasound, the gel can be applied to the back of the guidance pad to facilitate receiving ultrasound signals. In an example, the adhesive liquid can be an ultrasound gel.

At step 116, the tip of the instrument can be placed at the registration point. As mentioned, ports 24, 38 and 76 can act as registration points. Placement of the tip of the instrument at the registration point can register the instrument with the patient and the coordinate system of the surgical plan. However, other registration points on the guidance pad could be used.

At step 118, the tip of the instrument can be placed at an opening in the guidance pad in preparation for insertion into the patient.

At step 120, guidance indicia can be displayed on the guidance pad. As discussed, the guidance indicia can provide visual information relating to the location of the insertion instrument and the anatomy of the patient, as well as information relating to the surgical plan, such as the desired final orientation of the insertion instrument.

At step 122, the insertion instrument can be oriented according to the guidance indicia provided on the guidance pad. For example, the axis of the insertion instrument can be aligned along an axis shown in the guidance pad.

At step 124, the guidance information can be updated to show the location of the guidance instrument and to present updated placement instructions, if needed.

At step 126, the insertion instrument can be further guided into the patient according to the updated guidance information.

Steps 120 through 126 can be repeated as necessary to move the insertion instrument to the desired location.

At step 128, the top of the insertion instrument can reach the desired location, such as at the target anatomy where the surgical procedure is to be carried out.

At step 130, the surgical procedure can be carried out. For example, a guide wire can be placed through the insertion instrument and the insertion instrument can be removed. Subsequently, dilators can be placed through the access portal using the guide wire until the incision reaches a desired diameter for receiving a laparoscope tube. At which point, the surgical procedure can take place, such as by using an ablation device or fragmentation device to treat cancerous tissue or kidney stones.

At step 132, instruments used in placing the access portal, e.g, the guidance pad and the insertion needle, can be cleaned and sterilized for subsequent reuse, if configured as reusable devices.

The benefits of the systems and methods of the present disclosure can be in the form of, for example, 1) reduced time between access instrument placement and performance of the surgical procedure using the portal (incision) provided by the access instrument, 2) reduced reliance on interventional radiologists, 3) reducing the need for a second access portal to reach other areas of the patient's anatomy, 4) increased accuracy of access portal placement, 5) reducing the need for a second access portal for improperly placed first access portals, and 6) reduced reliance on real-time imaging systems during the access portal placement.

Various Examples and Notes

Example 1 is a guidance system for performing a percutaneous access incision, the guidance system comprising: an access needle comprising: a shaft; and a tip located at a distal end of the shaft; and a guidance pad comprising: a dermal side; an outward side; an opening to receive the access needle, the opening extending between the dermal side and the outward side; and a feedback device viewable from the outward side to provide an indication of a depth of the tip beneath the guidance pad and a trajectory of the shaft from the opening.

In Example 2, the subject matter of Example 1 optionally includes wherein the feedback device comprises: an arrangement of light emitters surrounding the opening.

In Example 3, the subject matter of Example 2 optionally includes wherein each of the light emitters of the array comprises a light emitting diode.

In Example 4, the subject matter of any one or more of Examples 2-3 optionally include wherein the light emitters of the array are laid out over a pattern having regular intervals.

In Example 5, the subject matter of Example 4 optionally includes wherein the regular intervals correspond to discrete lengths that the tip is located laterally from the opening.

In Example 6, the subject matter of any one or more of Examples 2-5 optionally include wherein each of the light emitters of the array has a variable brightness, wherein a brightness of each light emitter is configured to correspond to a distance of the tip below the guidance pad.

In Example 7, the subject matter of any one or more of Examples 2-6 optionally include wherein a plurality of the light emitters of the array has a variable color, wherein a color of each light emitter is configured to correspond to a distance of the tip below the guidance pad.

In Example 8, the subject matter of any one or more of Examples 1-7 optionally include wherein: the tip comprises a magnetic element; and each of the light emitters of the array includes a magnetic sensor.

In Example 9, the subject matter of any one or more of Examples 1-8 optionally include a controller integrated into the guidance pad, the controller configured to activate the feedback device to provide a visual indication of the depth of the tip and the trajectory of the shaft.

In Example 10, the subject matter of Example 9 optionally includes wherein the access needle comprises a proximity sensor readable by the controller.

In Example 11, the subject matter of any one or more of Examples 9-10 optionally include wherein the feedback device is configured to provide a representation of anatomy of a patient below the guidance pad.

In Example 12, the subject matter of Example 11 optionally includes wherein the feedback device is configured to provide a no-go zone in the representations of the anatomy of the patient below the guidance pad.

In Example 13, the subject matter of any one or more of Examples 11-12 optionally include wherein the feedback device comprises: a display screen surrounding the opening, wherein the controller is configured to operate the display screen to provide a visual indication of the depth of the tip and the trajectory of the shaft.

In Example 14, the subject matter of any one or more of Examples 9-13 optionally include wherein the access needle further comprises an ultrasound transducer in communication with the controller and configured to provide anatomic information to the feedback device.

Example 15 is a method for planning guidance of an access needle into a patient in preparation for a minimally invasive surgical procedure, the method comprising: determining a location for an access point on the patient; positioning a guidance pad over the access point; inserting a tip of the access needle through the pad; and displaying guidance information on the guidance pad.

In Example 16, the subject matter of Example 15 optionally includes wherein determining the location for the access point on the patient comprises plotting a trajectory for the access needle on imaging of the patient.

In Example 17, the subject matter of any one or more of Examples 15-16 optionally include wherein positioning the guidance pad over the access point comprises adhering the guidance pad to the patient.

In Example 18, the subject matter of any one or more of Examples 15-17 optionally include wherein inserting the tip of the access needle through the pad comprises: inserting the tip through an opening in the pad that surrounds the access point; and guiding the access needle into the patient according to the guidance information.

In Example 19, the subject matter of any one or more of Examples 15-18 optionally include wherein displaying guidance information on the guidance pad comprises displaying an indication of a depth of the tip beneath the guidance pad and a trajectory of the shaft from the access point.

In Example 20, the subject matter of Example 19 optionally includes wherein displaying the indication of the depth and the trajectory comprises: varying a color of individual light emitters of an array of light emitters of the guidance pad in response to movement of the tip below the pad, wherein the color of each light emitter is configured to correspond to a distance of the tip below the guidance pad.

In Example 21, the subject matter of any one or more of Examples 19-20 optionally include wherein displaying the indication of the depth and the trajectory comprises: varying a light intensity of individual light emitters of an array of light emitters of the guidance pad in response to movement of the tip below the pad, wherein the light intensity of each light emitter is configured to correspond to a distance of the tip below the guidance pad.

In Example 22, the subject matter of any one or more of Examples 19-21 optionally include wherein displaying the indication of the depth and the trajectory comprises: showing images on a display screen of the guidance pad corresponding to an orientation of the access needle.

In Example 23, the subject matter of Example 22 optionally includes emitting ultrasound signals from the access needle to generate anatomic information for display on the display screen.

In Example 24, the subject matter of any one or more of Examples 15-23 optionally include wherein displaying guidance information on the guidance pad comprises displaying anatomy of the patient relative to the guidance pad.

In Example 25, the subject matter of Example 24 optionally includes wherein displaying guidance information on the guidance pad comprises displaying no-go zones in the anatomy on the guidance pad.

Example 26 is a guidance pad for guiding an access needle into a patient in preparation for a minimally invasive surgical procedure, the guidance pad comprising: a dermal side; an outward side; an opening to receive the access needle, the opening extending between the dermal side and the outward side; and an array of light emitters surrounding the opening and viewable from the outward side to provide an indication of a depth of a tip of the access needle beneath the guidance pad and a trajectory of a shaft of the access needle from the opening, wherein each of the light emitters of the array has a variable property.

In Example 27, the subject matter of Example 26 optionally includes wherein the variable property comprises color or light intensity.

In Example 28, the subject matter of any one or more of Examples 26-27 optionally include wherein the variable property of each light emitter is configured to change according to a distance a magnetic object of the access needle is from the dermal side.

In Example 29, the subject matter of Example 28 optionally includes a magnetic field sensor associated with each of the light emitters of the array.

In Example 30, the subject matter of any one or more of Examples 26-29 optionally include a controller integrated into the guidance pad, the controller configured to: activate a first subset of the light emitters to provide a visual indication of no-go zones in anatomy of the patient; and activate a second subset of the light emitters to provide a visual indication of the depth of the tip and the trajectory of the shaft.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A guidance system for performing a percutaneous access incision, the guidance system comprising:

an access needle comprising:
a shaft;
a tip located at a distal end of the shaft; and
a sensor; and
a guidance pad comprising:
a dermal side;
an outward side;
an opening to receive the access needle, the opening extending between the dermal side and the outward side;
a feedback device viewable from the outward side to provide an indication of a depth of the tip beneath the guidance pad and a trajectory of the shaft from the opening, the feedback device comprising:
an array of a plurality of columns of light emitters, wherein:
each of the plurality of columns of light emitters extends along a radial axis extending through the opening;
each light emitter in the plurality of columns of light emitters is spaced apart from each other along one of the radial axes at an axial interval; and
the plurality of columns of light emitters are spaced apart from each other along circumferential intervals relative to the opening; and
a coordinate system displayed on the guidance pad and visible from the outward side, the coordinate system comprising a polar coordinate system having radially extending axes aligned along each of the plurality of columns;
wherein each light emitter in the plurality of columns of light emitters is responsive to alter a property of each light emitter in response to proximity to the sensor to provide an angle for one of the plurality of columns in the polar coordinate system and an axial distance along the one of the plurality of columns in the polar coordinate system.

2. The guidance system of claim 1, wherein each of the light emitters of the array comprises a light emitting diode.

3. The guidance system of claim 1, wherein the coordinate system indicating coordinates relative to a coordinate system obtained from imaging of a patient.

4. The guidance system of claim 1, wherein the property of each of the light emitters of the array comprises a variable brightness including on, off and a plurality of discrete brightness levels between on and off, wherein a brightness of each light emitter is configured to correspond to a straight-line distance of the tip below a plane of the guidance pad.

5. The guidance system of claim 1, wherein the property of each of the light emitters of the array comprises a variable color, wherein a color of each light emitter is configured to correspond to a distance of the tip below the guidance pad.

6. The guidance system of claim 1, wherein:
the sensor comprises a magnetic element; and
each of the light emitters of the array includes a magnetic sensor attached to the guidance pad such that each of the light emitters can be individually directly responsive to a location of the sensor.

7. The guidance system of claim 1, further comprising a controller integrated into the guidance pad, the controller configured to activate the feedback device to provide a visual indication of the depth of the tip and the trajectory of the shaft.

8. The guidance system of claim 7, wherein the access needle comprises a proximity sensor readable by the controller.

9. The guidance system of claim 7, wherein the feedback device includes an illustration of anatomy of a patient to be located below the guidance pad.

10. The guidance system of claim 9, wherein the feedback device is configured to provide a no-go zone in the illustration of the anatomy of the patient below the guidance pad.

11. The guidance system of claim 9, wherein the feedback device comprises:
a display screen surrounding the opening, wherein the controller is configured to operate the display screen to provide a visual indication of the depth of the tip and the trajectory of the shaft.

12. The guidance system of claim 7, wherein the access needle further comprises an ultrasound transducer in communication with the controller and configured to provide anatomic information to the feedback device.

13. The guidance system of claim 1, wherein the coordinate system is registered to a surgical plan.

14. The guidance system of claim 1, wherein the coordinate system is scaled to the array of the plurality of columns of light emitters to provide actual position and depth values.

15. The guidance system of claim 1, wherein the plurality of columns of light emitters comprises sixteen columns and each column of the plurality of columns of light emitters includes five light emitters.

16. The guidance system of claim 1, wherein there is a gap between adjacent light emitters in the array of the plurality of columns of light emitters.

17. A method for planning guidance of an access needle into a patient in preparation for a minimally invasive surgical procedure, the method comprising:
determining a location for an access point on the patient, the access point for receiving the access needle, the access needle comprising:
a shaft;
a tip located at a distal end of the shaft; and
a sensor;
positioning a guidance pad over the access point, the guidance pad comprising:
a dermal side;
an outward side;
an opening to receive the access needle, the opening extending between the dermal side and the outward side;
a feedback device viewable from the outward side to provide an indication of a depth of the tip beneath the guidance pad and a trajectory of the shaft from the opening, the feedback device comprising:
an array of a plurality of columns of light emitters, wherein:
each of the plurality of columns of light emitters extends along a radial axis extending through the opening;
each light emitter in the plurality of columns of light emitters is spaced apart from each other along one of the radial axes at an axial interval; and
the plurality of columns of light emitters are spaced apart from each other along circumferential intervals relative to the opening; and
a coordinate system displayed on the guidance pad and visible from the outward side, the coordinate system comprising a polar coordinate system having radially extending axes aligned along each of the plurality of columns;
wherein each light emitter in the plurality of columns of light emitters is responsive to alter a property of each light emitter in response to proximity to the sensor to provide an angle for one of the plurality of columns in the polar coordinate system and an axial distance along the one of the plurality of columns in the polar coordinate system;

inserting the tip of the access needle through the guidance pad; and displaying guidance information on the guidance pad.

18. The method of claim 17, wherein determining the location for the access point on the patient comprises plotting a trajectory for the access needle on imaging of the patient.

19. The method of claim 17, wherein positioning the guidance pad over the access point comprises adhering the guidance pad to the patient.

20. The method of claim 17, wherein inserting the tip of the access needle through the guidance pad comprises:

inserting the tip through an opening in the guidance pad that surrounds the access point; and guiding the access needle into the patient according to the guidance information.

21. The method of claim 17, wherein displaying guidance information on the guidance pad comprises displaying an indication of a depth of the tip beneath the guidance pad and a trajectory of the access needle from the access point.

22. The method of claim 21, wherein displaying the indication of the depth and the trajectory comprises:

varying a color of individual light emitters of an array of light emitters of the guidance pad in response to movement of the tip below the guidance pad, wherein the color of each light emitter is configured to correspond to a distance of the tip below the guidance pad.

23. The method of claim 21, wherein displaying the indication of the depth and the trajectory comprises:

varying a light intensity of individual light emitters of an array of light emitters of the guidance pad in response to movement of the tip below the guidance pad, wherein the light intensity of each light emitter is configured to correspond to a distance of the tip below the guidance pad.

24. The method of claim 21, wherein displaying the indication of the depth and the trajectory comprises:

showing images on a display screen of the guidance pad corresponding to an orientation of the access needle.

25. The method of claim 24, further comprising emitting ultrasound signals from the access needle to generate anatomic information for display on the display screen.

26. The method of claim 17, wherein displaying guidance information on the guidance pad comprises displaying anatomy of the patient relative to the guidance pad.

27. The method of claim 26, wherein displaying guidance information on the guidance pad comprises displaying no-go zones in the anatomy on the guidance pad.

28. A guidance system for performing a percutaneous access incision, the guidance system comprising:

an access needle comprising:
 a shaft;
 a tip located at a distal end of the shaft; and
 a sensor; and a guidance pad comprising:
 a dermal side;
 an outward side;
 an opening to receive the access needle, the opening extending between the dermal side and the outward side;
 a feedback device viewable from the outward side to provide an indication of a depth of the tip beneath the guidance pad and a trajectory of the shaft from the opening, the feedback device comprising:
  an array of a plurality of columns of light emitters, wherein:
   each of the plurality of columns of light emitters extends along a radial axis extending through the opening;
   each light emitter in the plurality of columns of light emitters is spaced along one of the radial axes at an axial interval; and
   the plurality of columns of light emitters are spaced along circumferential intervals relative to the opening; and
 a coordinate system displayed on the guidance pad and visible from the outward side, the coordinate system comprising a polar coordinate system having radially extending axes aligned along each of the plurality of columns;

wherein each light emitter in the plurality of columns of light emitters is responsive to alter a property of each light emitter in response to proximity to the sensor to provide an angle for one of the plurality of columns in the polar coordinate system and an axial distance along the one of the plurality of columns in the polar coordinate system;

wherein the property of each of the light emitters of the array comprises a variable brightness including on, off and a plurality of discrete brightness levels between on and off, wherein a brightness of each light emitter is configured to correspond to a straight-line distance of the tip below a plane of the guidance pad.

* * * * *